United States Patent
Lutgendorf (10) Patent No.: US 9,448,222 B2
(45) Date of Patent: Sep. 20, 2016

(54) METHOD AND SYSTEM FOR PROVIDING AN ASSEMBLY OF AN AMOUNT OF USED PLASTIC MATERIAL AND AN INFORMATION CARRIER CARRYING QUALITY DATA OF THE AMOUNT

(75) Inventor: Pieter Hendrik Lutgendorf, VC Staphorst (NL)

(73) Assignee: Wavin B.V., CW Zwolle (NL)

( * ) Notice: Subject to any disclaimer, the term of this patent is extended or adjusted under 35 U.S.C. 154(b) by 50 days.

(21) Appl. No.: 14/128,752

(22) PCT Filed: Jul. 13, 2012

(86) PCT No.: PCT/EP2012/063835
§ 371 (c)(1),
(2), (4) Date: Mar. 20, 2014

(87) PCT Pub. No.: WO2013/001101
PCT Pub. Date: Jan. 3, 2013

(65) Prior Publication Data
US 2014/0202268 A1    Jul. 24, 2014

(30) Foreign Application Priority Data

Jun. 29, 2011  (NL) ..................................... 1038906

(51) Int. Cl.
*G01N 33/44* (2006.01)
*B29B 17/00* (2006.01)
(Continued)

(52) U.S. Cl.
CPC ............. *G01N 33/442* (2013.01); *B29B 17/00* (2013.01); *B29B 2017/0089* (2013.01); *B29K 2105/0094* (2013.01); *B29K 2105/065* (2013.01); *Y02W 30/62* (2015.05)

(58) Field of Classification Search
None
See application file for complete search history.

(56) References Cited

U.S. PATENT DOCUMENTS 5,448,074 A    9/1995    Seagro, Jr.
5,872,205 A    2/1999    Balke et al.
(Continued)

FOREIGN PATENT DOCUMENTS

DE    10 2006 059 321 A1    6/2008
EP        0530934 A1    10/1993
(Continued)

OTHER PUBLICATIONS

European Standard EN15343, "Plastics—Recycled Plastics—Plastics recycling traceability and assessment of conformity and recycled content", EP Committee for Standardization, 2007.
(Continued)

*Primary Examiner* — Robert R Raevis
(74) *Attorney, Agent, or Firm* — Wolf, Greenfield & Sacks, P.C.

(57) ABSTRACT

Method for providing an assembly of an amount of used plastic material and an information carrier carrying data of at least one quality property of the amount of used plastic material, wherein providing the data of the at least one quality property comprises at least once: providing a predetermined amount of used plastic material; labelling the predetermined amount of used plastic material; and determining at least one quality property of the predetermined amount of used plastic material. A system for providing an assembly of an amount of used plastic material and data of at least one quality property of the amount of used plastic material, wherein the system comprises: a feeder for providing used plastic material; at least one quantity measuring system; a rheology measuring system; and an information carrier.

15 Claims, 7 Drawing Sheets

(51) Int. Cl.
 *B29K 105/00* (2006.01)
 *B29K 105/06* (2006.01)

(56) References Cited

U.S. PATENT DOCUMENTS

| | | | |
|---|---|---|---|
| 6,533,124 | B1 | 3/2003 | Tacito et al. |
| 7,968,022 | B1 | 6/2011 | Brooks et al. |
| 2005/0127285 | A1 | 6/2005 | Kampf et al. |
| 2007/0068553 | A1 | 3/2007 | Friedlaender et al. |
| 2008/0150701 | A1* | 6/2008 | Randmae .................... 340/10.5 |

FOREIGN PATENT DOCUMENTS

| | | |
|---|---|---|
| EP | 0 902 285 A1 | 3/1999 |
| FR | 2752178 A1 | 2/1998 |
| JP | S60/209141 A | 10/1985 |
| JP | H10/259254 A | 9/1998 |
| JP | 2002/059021 A | 2/2002 |
| JP | 2008/112454 A | 5/2008 |
| JP | 2010/234812 A | 10/2010 |
| JP | 2011/236340 A | 11/2011 |

OTHER PUBLICATIONS

European Standard EN15344, "Plastics—Recycled Plastics—Characterisation of Polyethylene (PE) recyclates", EP Committee for Standardization, 2007.

Stella Desa, Thesis "Quality Monitoring of Recycled Plastic Waste During Extrusion: In-Line Particle Detection", 1995.

* cited by examiner

METHOD AND SYSTEM FOR PROVIDING AN ASSEMBLY OF AN AMOUNT OF USED PLASTIC MATERIAL AND AN INFORMATION CARRIER CARRYING QUALITY DATA OF THE AMOUNT

CROSS-REFERENCE TO RELATED APPLICATIONS

This application is a national stage filing under 35 U.S.C. §371 of international application PCT/US2012/063835, filed Jul. 13, 2012, which claims the benefit to Netherlands application no. 1038906, filing date Jun. 29, 2011 the disclosure of which is incorporated by reference herein in its entirety.

The invention is related to a method for providing an assembly of an amount of used plastic material and an information carrier carrying data of at least one quality property of the amount of used plastic material. The invention is further related to a system for providing an assembly of an amount of used plastic material and an information carrier carrying data of at least one quality property of the amount of used plastic material. The invention is further related to an assembly of an amount of used plastic material and an information carrier carrying data of at least one quality property of the amount of used plastic material. Instead of referring to "used plastic material", one may also refer to a recyclate, or more specifically to plastic recyclate.

BACKGROUND OF THE INVENTION

Re-using used plastic material is often referred to as recycling of plastic waste material. It comprises use of post-industrial waste (material which is generated in the course of an industrial manufacturing process) as well as post-use waste (manufactured material which have been used and disposed). Recycling has advantages. For instance: less "virgin" raw materials are needed, less use of water is needed, and less energy is needed, as compared with producing plastic material for its first use. Also harmful emissions into air, water and soil, as well as any detrimental impacts on human health, may be minimized if plastic waste material can be recycled.

However, it is possible that in its previous use, plastic waste material has become contaminated with other materials. This applies particularly to plastic materials used by consumers, and disposed as waste material. In an attempt to optimize recycling processes, efforts are often made to selectively mix materials, or remove materials, so as to optimize the suitability of the recycled material for its next usage. With this objective in mind, recyclers use various known techniques like: manual sorting, sinking-floating in tanks, metal sorting techniques, wind sifting, electrostatic sorting, melt filtration, etc. Despite these sorting and mixing techniques, the plastic materials resulting from the recycling have material characteristics which tend to vary widely.

Many products made of plastic, like pipes, window profiles, etc., require material characteristics within specific and relatively narrow ranges to guarantee that the (semi)finished products will fulfil their product standards. The properties of used plastic materials, particularly post-consumer materials, vary currently still too much to allow for optimal re-use of such materials. This inhibits the feasibility of mechanical recycling of plastic waste. Processing such materials to further obtain a better quality, is often still too expensive for a low end application.

For this reason, incineration or landfill is often still the only economical way of disposing of such waste material, even though it is from an environmental point of view highly undesirable.

The present invention aims to provide a simple and straightforward method and system that allows for more economically and environmentally acceptable use of plastic material waste.

SUMMARY OF THE INVENTION

The invention provides a method for providing an assembly of an amount of used plastic material and an information carrier carrying data of at least one quality property of the amount of used plastic material. Providing the data of the at least one quality property comprises at least once; providing a predetermined amount of used plastic material; labelling the predetermined amount of used plastic material; and determining at least one quality property of the predetermined amount of used plastic material, based on method steps for quality assessment. Such method steps for quality assessment comprise: measuring rheology properties of a sample of the predetermined amount of used plastic material to obtain rheology data and/or measuring impurity properties of a sample to obtain impurity data; providing the rheology data and/or the impurity data on an information carrier; and labelling the information carrier in a way which corresponds to a labelling of the predetermined amount of used plastic material. Providing rheology data and impurity data allows in most cases for deciding for which further processing and/or for which end product the material is suited. Obtaining data of rheology properties and of impurity properties of a sample of the predetermined amount of used plastic material is not very time-consuming and can be done automatically. Current processing of used plastic material hardly needs to be interrupted, if at all, to extract data on the quality of a predetermined amount of such used plastic material.

In general, it applies that providing data may take place in the form of indicating that a property has been quantified and been found to be within a predetermined range of values. The data may thus be provided as lying within a certain "bandwidth".

The labelling of both the predetermined amount of used plastic material and the information carrier in a corresponding way, ensures that this information about the predetermined amount of used plastic material is easily available and can easily be used when a decision has to be made as to for what purpose the used plastic material can be re-used. The method can be carried out fast and reliably. This optimizes the possibility to re-use the used plastic material, and as such reduces the need for incineration or landfill. Furthermore, on the basis of that information, it will be possible to determine the cost price for the predetermined amount of used plastic material, should this be sold, or to determine a value of the predetermined amount of used plastic material, should it be used for further internal purposes.

The predetermined amount can be determined on the basis of one or some of a large number of factors. It can simply be determined on the basis of the size of a completely filled-up container in which the used plastic material is stored. It is also possible to isolate a predetermined amount of used plastic material out of a continuous flow of used plastic material. An upper limit of the amount can in such a case be determined in relation to the maximum size of a sample thereof. It is then useful to take into account which sample size still provides reliable information about a predetermined amount, without affecting too much the actual amount as predetermined. The accuracy of the property measurements carried out on the sample can be taken into account. In any case, the phrase "predetermined" is meant to be interpreted as determined before the rheology properties and/or impurity properties are being measured. "Predetermined" does not necessarily mean that the amount is registered before measuring these properties.

In an embodiment of a method according to the invention, measuring rheology properties comprises measuring during extrusion of the sample into an extruded sample at least one of the group consisting of: the mass pressure of the sample; the mass temperature of the sample and the shear and/or flow properties of the sample. Advantageously, pressure, temperature and shear and/or flow properties of the sample can easily be measured when the sample is being extruded in an extruder. Most extruders are already equipped with devices for measuring such properties. The shear and/or flow properties of the sample can, for instance, be measured by measuring the torque of the motor used for driving the one or more extruder screws. The pressure and temperature of the sample are often measured for establishing when the sample is in a suitable condition for being extruded. A further advantage of extruding the sample into an extruded sample is that the extruded sample can more easily be used for measuring impurity properties of the sample.

In an embodiment of a method according to the invention, measuring impurity properties comprises at least one of the group consisting of: counting in the sample or in the extruded sample in an area of a predetermined size the number of contamination particles; and/or obtaining a particle-sized distribution of contamination particles in an area of a predetermined size in the sample or in the extruded sample; measuring in the sample or in the extruded sample in an area of a predetermined size the volume, and/or area and/or length of contamination particles, obtaining a number for the degree of contamination. This is a suitable way of determining the impurity properties of the sample. It can be done fully automatically on the basis of a camera and an image analysis programme, both well-known in the art. The number of contamination particles and/or the particle-size distribution of contamination particles determine to a large extent the usability of the predetermined amount of used plastic material. A number for the degree of contamination can, for instance, be expressed as a percentage of the volume that is occupied by contamination or, for instance, in parts per million (ppm).

In an embodiment of a method according to the invention, providing the predetermined amount of used plastic material comprises isolating a predetermined amount of used plastic material out of a continuous flow of used plastic material. In these embodiments, the assembly of the amount of used plastic material and an information carrier carrying data of at least one quality property of that amount of used material, can be done in line, without interrupting in a significant way, a flow of used plastic materials. This ensures that the method can be applied to recycling processes already existing and in operation, and it equally ensures that applying the method according to the invention is not necessarily introducing a serious slow-down in the production of output.

In an embodiment of a method according to the invention, the method comprises storing the predetermined amount temporarily in one or more buffers during measuring rheology and/or impurity properties of the sample of the predetermined amount. This ensures that the predetermined amount of used plastic material remains constant and cannot be altered during the measurements, to the benefit of the reliability of the quality data. Having a number of such buffers has further advantages, and can be applied in different ways, as will both be discussed in the more detailed explanation of the invention as provided below.

In an embodiment of a method according to the invention, the amount of used plastic material of the assembly corresponds to one times the predetermined amount of used plastic material. This provides for a very straightforward way of providing an amount of used plastic material, where no risk exists in muddling up information carriers and predetermined amounts of used plastic material.

In an embodiment of a method according to the invention, providing an amount of used plastic material comprises putting together a number of predetermined amounts of used material of which at least one quality property has been determined. The at least one quality property is for each of the predetermined amounts based on the method steps for quality assessment. This allows for providing an amount of used plastic material that is based on a mixture of one or more predetermined amounts of used material. In other words, the method not necessarily means that amounts of used plastic material can only be provided in an amount that is still just about possible to ensure a reliable measurement of quality properties based on a sample of that predetermined amount. It is possible that a number of predetermined amounts having the same quality properties are put together, and for instance, mixed. In practice, predetermined amounts are preferably sorted on the basis of a quality property. That is, predetermined amounts having a quality property within a predetermined range are put together. However, it is also possible that, deliberately, predetermined amounts having very different quality properties, i.e. falling within different predetermined ranges, are blended together to obtain a desired property of the total amount of used plastic material.

In an embodiment of a method according to the invention, providing the data of at least one quality property of the amount of used plastic material comprises using the rheology data and/or the impurity data on the information carrier as available for each predetermined amount that is used for providing the amount of used plastic material. The amount of used plastic material may be much larger than the maximum possible predetermined amount of used plastic material. It is possible to have for a large amount of used plastic material at least one quality property known, to facilitate taking decisions as to what can be done with that large amount of material.

In an embodiment of a method according to the invention, the rheology data and/or the impurity data are expressed in terms of possible use of the amount of used plastic material. The possible use is based on a predetermined relationship between such use and the rheology data and/or the impurity data. This allows for a more direct way of expressing the possible use of the used plastic material, so that also less sophisticated re-users can decide to buy on the basis of that information an amount of used plastic material. Furthermore, determining the value and/or cost price of that amount of used plastic material may more easily be determined.

In an embodiment of a method according to the invention, the amount of used plastic material is provided in the form of at least one product having a shape which is different from each predetermined amount of used plastic material. In other words, a product made on the basis of the amount of used plastic material is also considered to be a product of a method according to the invention. It may still be useful that the information carrier carrying data of least one quality property of the amount of used plastic material is available, so that for a possible further re-use of the amount of used plastic material, i.e., a second time of recycling the plastic material, the history of the used plastic material can be taken into account.

The invention further provides a system for providing an information carrier carrying an assembly of an amount of used plastic material and data of at least one quality property of the amount of used plastic material. The system comprises a feeder for providing used plastic material. The system further provides at least one quantity measuring system for obtaining a predetermined amount of used plastic material and for labelling the predetermined amount of used plastic material. The system also comprises a rheology measuring system for measuring rheology properties of the sample to obtain rheology data and/or an impurity measuring system for measuring impurity properties in the sample to obtain impurity data. The system further comprises an information carrier for carrying the rheology data and/or the impurity data and for labelling the respective data in correspondence with the labelling of the predetermined amount of used plastic material.

The feeder can form a downstream end of a material storage system, a downstream end of a recycling processing system, or an upstream end of a production system. Where the feeder forms a downstream end, it may comprise an outlet of a continuous supply line, or an outlet of a recycling system which sorts, mixes, upgrades or downgrades waste material. Where the feeder forms an upstream end of a production system, it may be part of a quality control system aimed to assess the quality of input material, so that process parameters can be set on the basis of the data of at least one quality property of the input material. The feeder may also be the opening of a container or a plastic bag in which the used plastic material is contained.

The quantity measuring system for obtaining a predetermined amount of used plastic material and for labelling the predetermined amount of used plastic material may comprise one or more buffer containers. Filling such a container to a predetermined level may correspond to obtaining a predetermined amount of used plastic material. The position, name or number of the container may correspond to labelling the predetermined amount of used plastic material. In general, labelling the predetermined amount is meant to be understood as facilitating the registration, somehow, of the location and/or identification of the predetermined amount of used plastic material and of the knowledge obtained about quality properties of that amount of used plastic material.

The rheology measuring system may be arranged for extruding the sample into an extruded sample and for measuring rheology properties on the basis of the mass pressure of the sample, the mass temperature of the sample and/or the shear/flow properties of the sample.

The impurity measuring system may be arranged for measuring at least one of the impurity qualities of the group consisting of: a number of contamination particles in an area of a predetermined size in the sample or in the extruded sample; and a particle sized distribution of contamination particles in the sample in an area of a predetermined size in the extruded sample; the volume and/or area and/or length of contamination particles; a number for the degree of contamination. The impurity measuring system may, for that purpose, comprise a camera and an image analysis system.

The system may further comprise a blender for blending a number of predetermined amounts of used material of which at least one quality property has been determined.

The invention further provides an assembly of an amount of used plastic material and an information carrier carrying data of at least one quality property of the amount of used plastic material, the at least one quality property being based on rheology properties and/or impurity properties.

Embodiments of such an assembly may comprise a container filled up to a predetermined level with an amount of used plastic material and a label on the container revealing data of rheology properties and/or impurity properties of the amount of used plastic material held in the container. The label labels as such the amount of used plastic material and labels as such the data on rheology properties and/or impurity properties of the amount of used plastic material. However, it is of course also possible that the assembly is provided in terms of an amount of used plastic material and data stored in a computer system. Such data may reveal the position of the amount and as such form a label therefor. These data may, labelled by the position data, also reveal data of at least one quality property of that amount of used plastic material. It is to be noted that the quantity of the amount of used plastic material does not necessarily need to be known. However, the data of rheology properties and/or of impurity properties are on the basis of appropriate relationships between the size of the sample and the size of the predetermined amounts from which the samples are obtained. The data of at least one quality property may comprise a possible use of the amount of used plastic material. This can be based on a predetermined relationship between data of rheology properties and/or impurity properties and such possible uses. A reference to a possible use of the amount of used plastic material can facilitate its speedy use and selling or buying of the amount of used plastic material. Also the price and/or value of the amount used plastic material can more easily be assessed.

It is further possible that the amount of used plastic material is provided in the form of at least one product having a shape suitable for repeated use of that at least one product. This may be an end product, such as a pipe, or another device used in management of flowable media, produced out of the amount of used plastic material.

The invention will now further be explained with the aid of a description of a non-limiting example. This will be done with a reference to a drawing, in which:

FIG. 4b shows a top view of a part shown in FIG. 4a;

Figure 6:
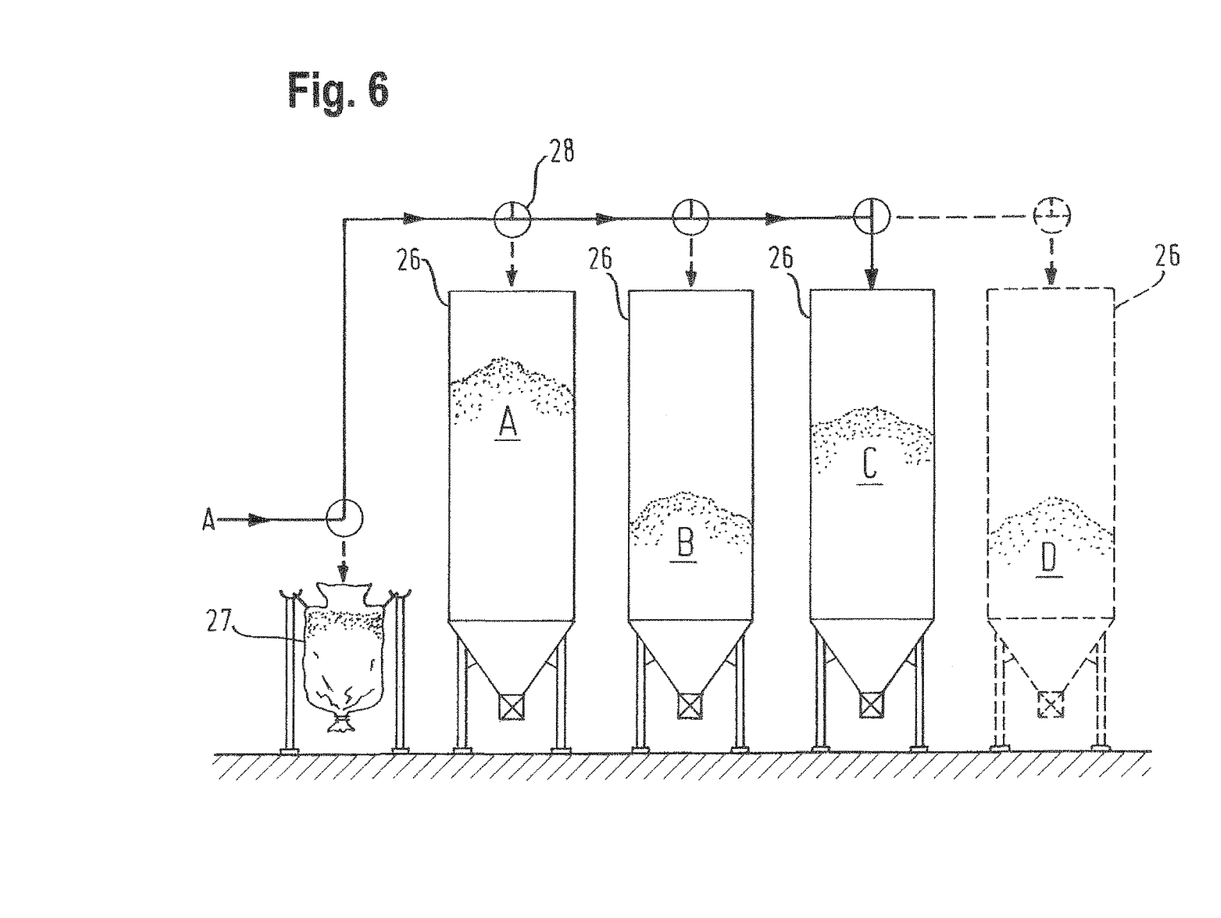
FIG. 6 shows schematically an end-part of an embodiment of a system according to the invention.
Figure 7:
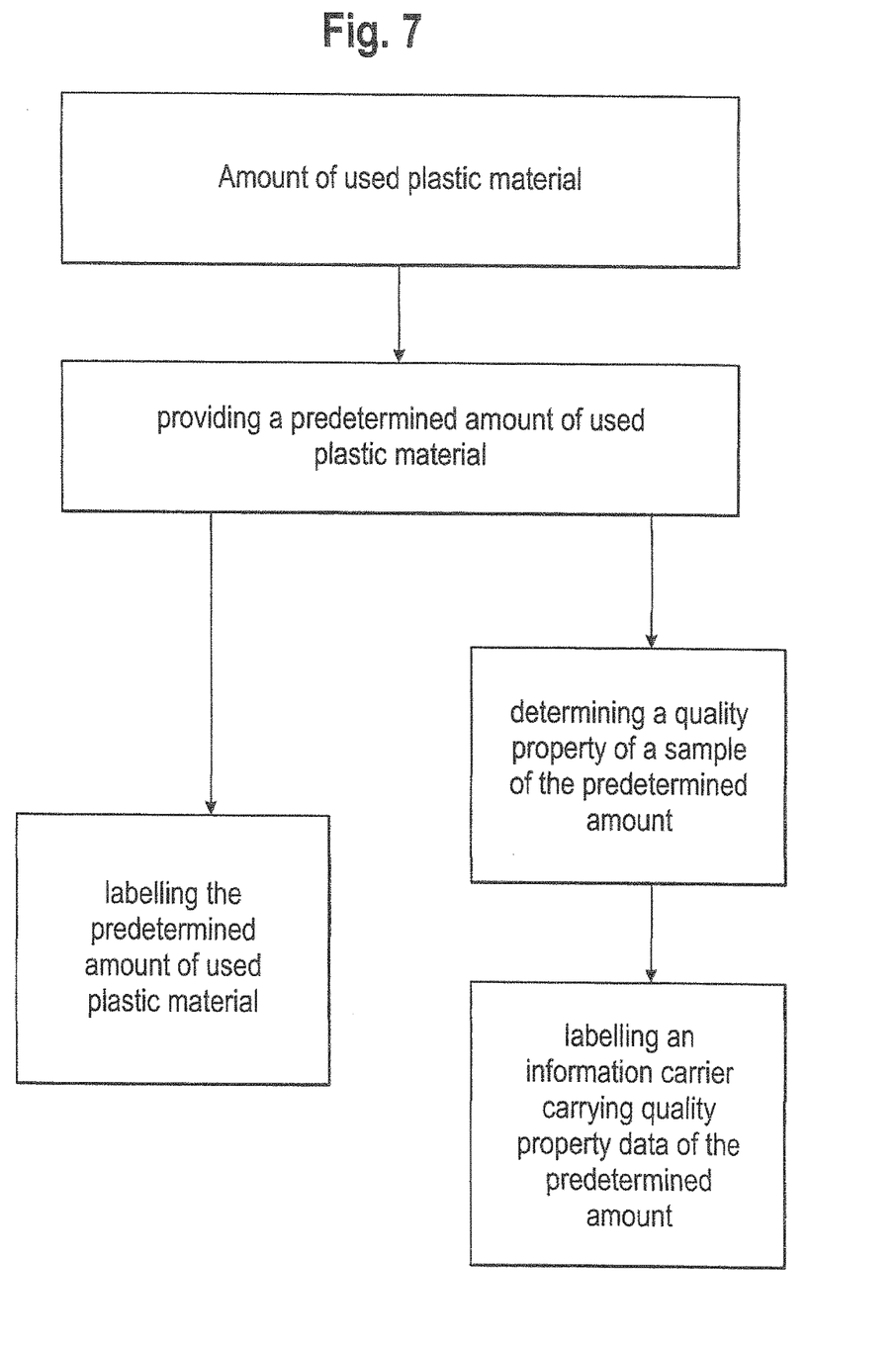
FIG. 7 shows schematically a flow diagram of an embodiment of the invention.

In the drawing, like features are referred to by like references. FIGS. 1-6 show parts, sometimes alternatives to each other, of embodiments of a system according to the invention and illustrates a way of carrying out a method according to the invention. An assembly according to the invention is also displayed in the drawing. FIG. 7 shows in a self-explanatory way an embodiment of the invention, to assist the reader in swiftly grasping an underlying concept of the invention.

The system is for providing an assembly of an amount of used plastic material and an information carrier which is carrying data of at least one quality property of the amount of used plastic material. Although the example shown displays the system at the end of a recycling system where used plastic material has been processed (sorted, mixed, purified etc.), it is equally possible that the system is elsewhere positioned, for instance at the beginning of the production system of an end-user.

Figure 1:
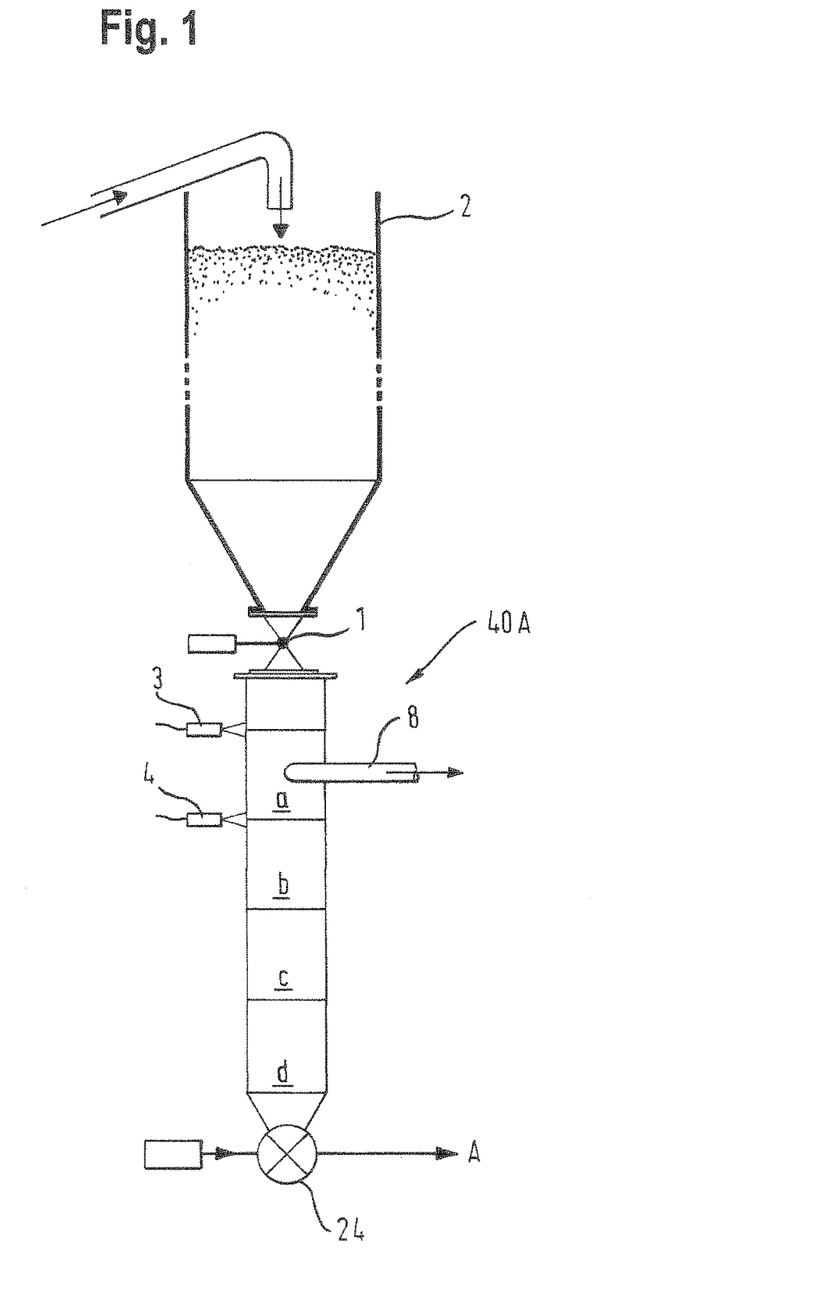
FIG. 1 shows schematically a part of a first embodiment of a system according to the invention.

In any case, the system according to the invention comprises a feeder for providing used plastic material. A temporary storage of used plastic material, also referred to as silo 2, provided with valve 1 is an example of a feeder for providing used plastic material. The system further comprises a quantity measuring system for obtaining a predetermined amount of used plastic material and for labelling the predetermined amount of used plastic material. FIG. 1 shows schematically a first example of such a quantity measuring system. A vertical configuration of a so-called quarantine buffer 40A is shown. The buffer 40A may be provided with level detectors 3 and 4 for controlling the quantity of the stored amount of used plastic material. Level detectors 3 and 4 each operate for instance on the basis of a photo cell which detects the presence of material in the quarantine buffer 40A. Material present between detectors 3 and 4 may be one buffered portion of used plastic material. Quarantine buffer 40A contains four portions a, b, c and d. Each portion a, b, c and d may correspond to a predetermined amount of used plastic material. The system may operate fully automatically. For controlling purposes, information may be made available in a computer, for instance that the quarantine buffer 40A is filled up with four portions, i.e. predetermined amounts of used plastic material a, b, c, d, and these predetermined amounts may be labelled by referring in the computer to those portions. Control system 19, shown in FIGS. 5 and 6 to be discussed later, is an example of such a computer. However, also the physical presence of the buffered portions a, b, c, d in spatially different positions, may be seen as a form of labelling the predetermined amounts of used plastic material.

Figure 2:
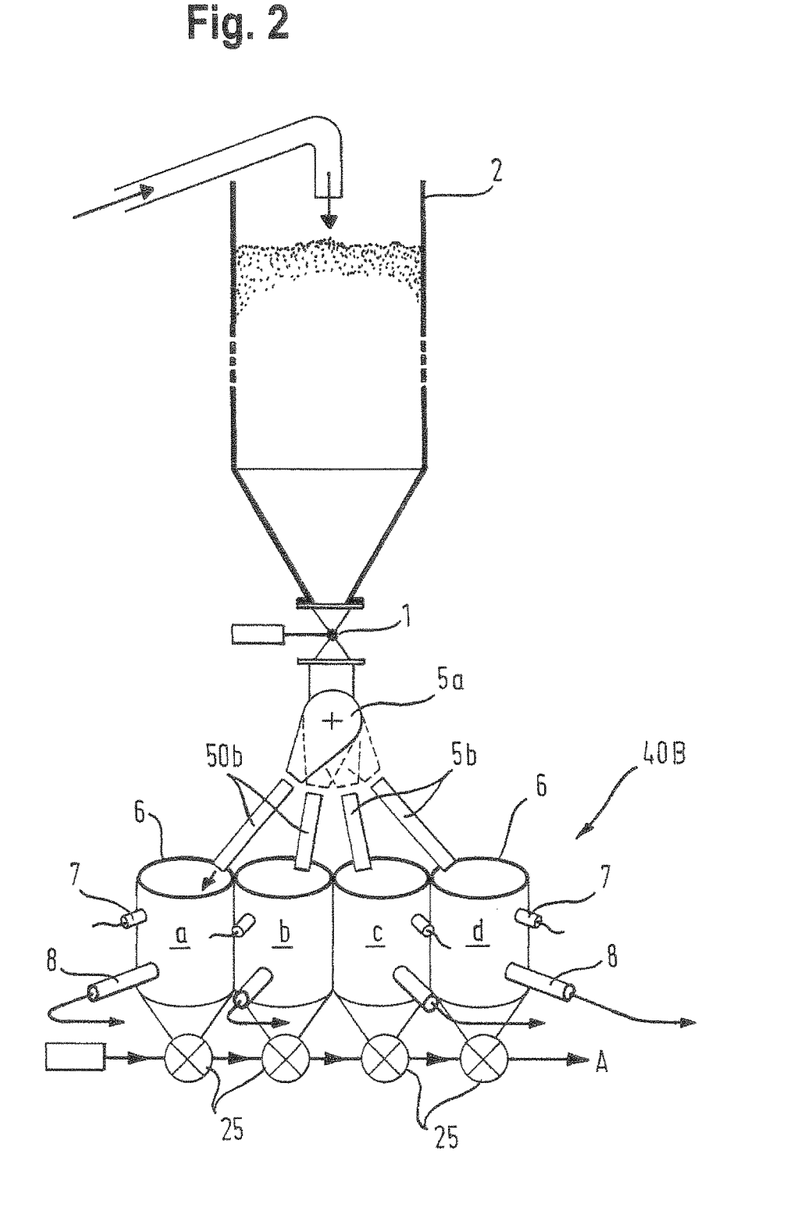
FIG. 2 shows schematically a part of a second embodiment of a system according to the invention.

FIG. 2 shows schematically, another example of a quantity measuring system for obtaining a number of predetermined amounts of used plastic material and for labelling the predetermined amounts. Displaced is a so-called quarantine buffer 40E having a horizontal configuration. In this configuration, each portion, i.e. each predetermined amount a, b, c, d is temporarily stored in a separate container. In a system according to the invention using such a horizontally configured quarantine buffer 40E, the feeder may be provided with a four-positions-valve 5a and with four chutes 5b for filling the respective containers. Level detectors 7 are provided for determining when the respective container is full. Advantageously, no mixing between the portions (predetermined amounts a, b, c, d) can take place. Again, control system 19 shown in FIG. 5 may store information of the whereabouts of the respective predetermined amounts and as such also be part of the quantity measuring system for labelling each predetermined amount of used plastic material.

Figure 3:
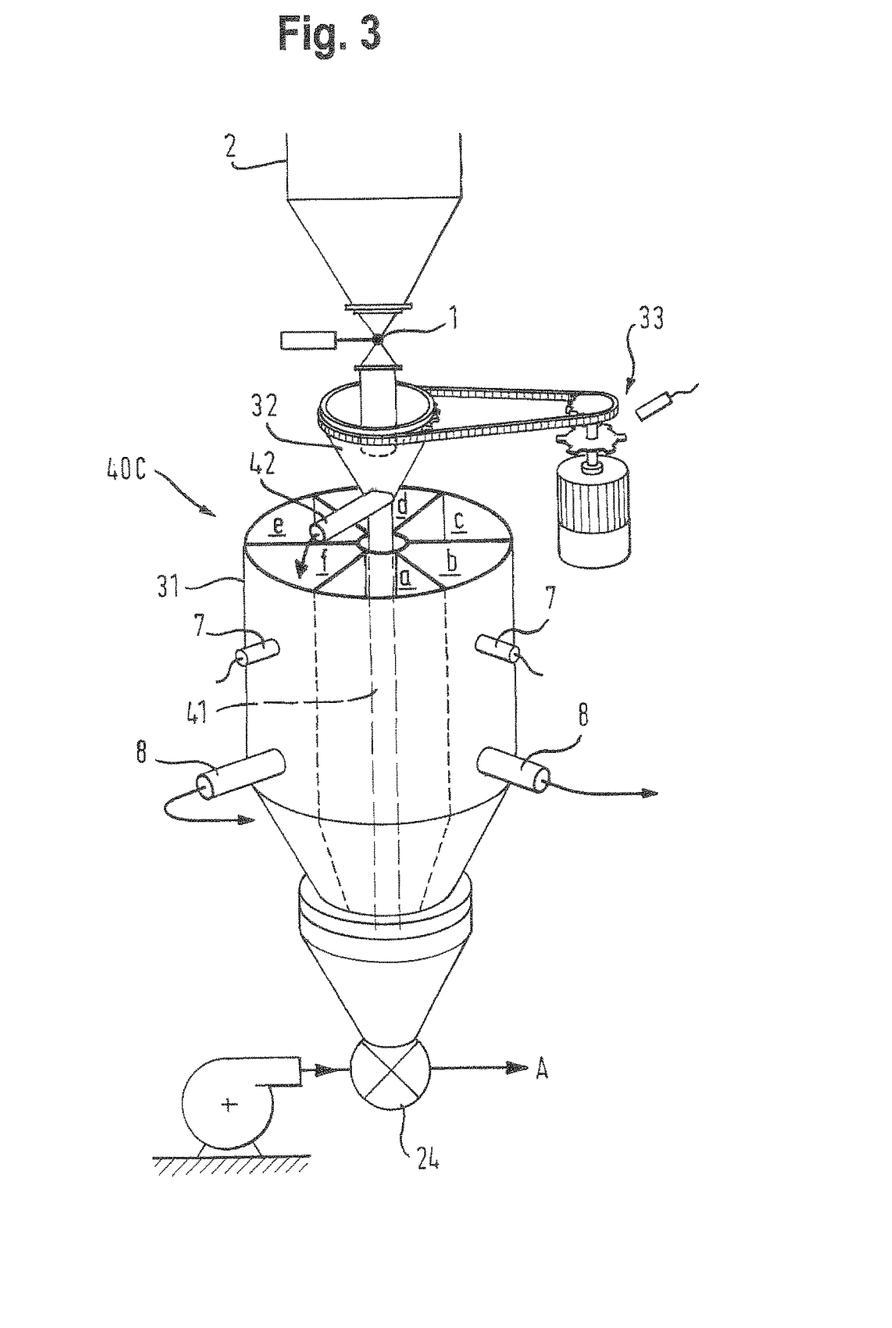
FIG. 3 shows schematically a part of a third embodiment of a system according to the invention.

FIG. 3 shows schematically another example of a quantity measuring system for obtaining a predetermined amount of used plastic material and for labelling the predetermined amount of used plastic material.

In this example, the quarantine buffer 40C has a horizontal configuration in a circular set up. The predetermined amounts of plastic material are each kept in an individual sector of circular buffer 31. In this example there are six individual sectors a, b, c, d, f. A central shaft 41 extends through the centre of the buffer 31. The shaft has a funnel 32 at the top end. The funnel 32 is at a downstream end thereof provided with an outlet 42. By means of a position controlling device 33, the shaft 32 can be rotated so that the outlet points into one of the sectors a, b, c, d, f. Each sector is again provided with a detector 7 for establishing the presence of material at the level of that detector 7. It is conceivable that the positioning of the detector can be altered in height, so that there is some flexibility in the setting of the predetermined amount of used plastic material ending up in a particular sector. At the bottom end of the shaft 41a valve 34 is mounted for releasing the predetermined amount of used plastic material kept in a particular sector. A possible relative position of outlet 42 and open position of valve 34 follows more clearly from FIG. 4a as well as from FIG. 4b, the latter providing a top view as seen when looking into the direction of arrow IVb. Clearly, the sector which has been filled, can at the same time not also be emptied. Again the filling of the sector a, b, c, d, e, f and the emptying thereof may be controlled by control system 19, also for (further) labelling the predetermined amount of used plastic material.

Figure 5:
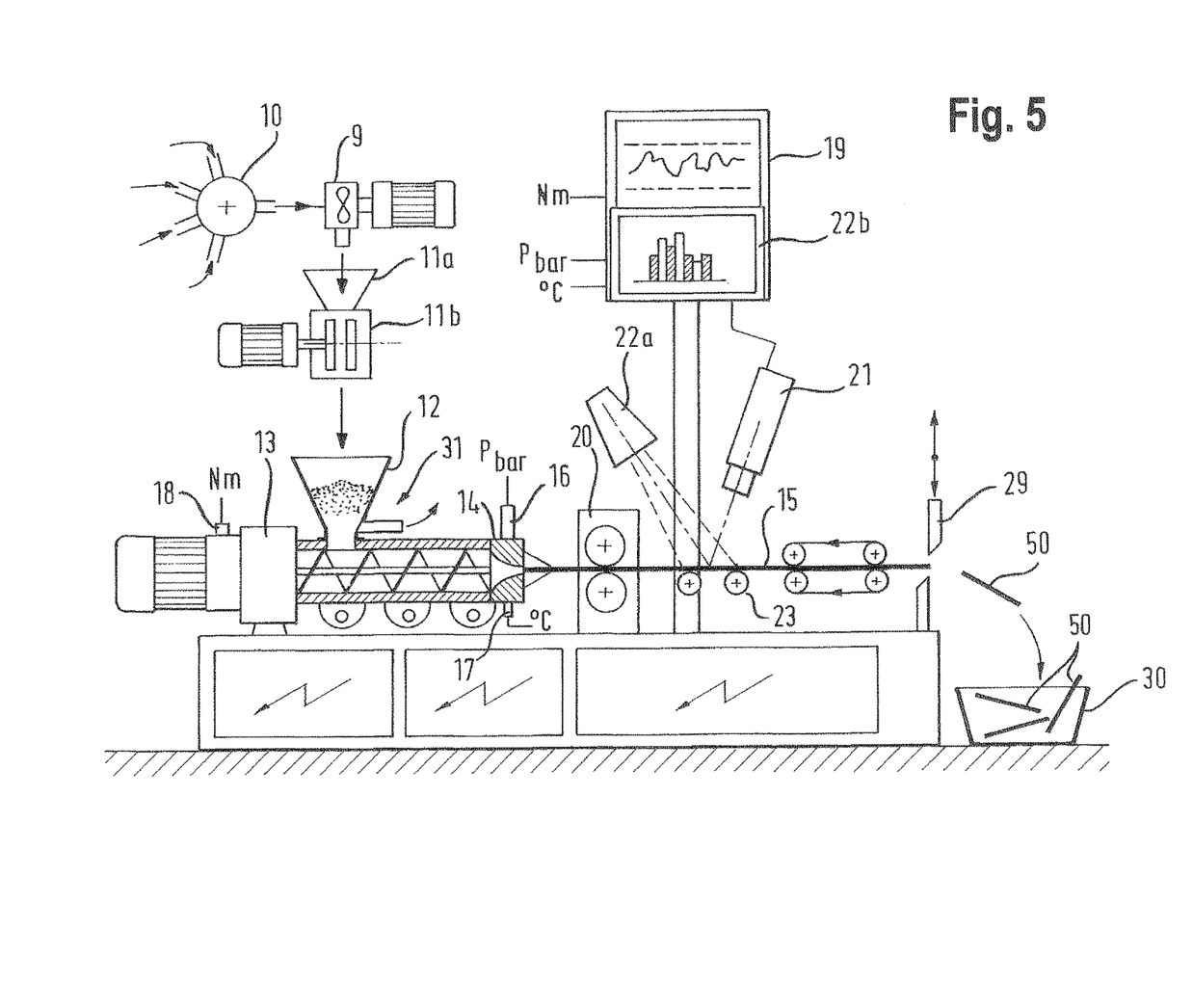
FIG. 5 shows schematically a part of an embodiment of a system according to the invention.

Each of the configurations of the buffer 40A, 40B, 40C, may be provided with a hole 8 in the wall of the respective container, for connecting up with a vacuum pump 9 (shown in FIG. 5). The vacuum pump may be provided with a multi-position valve 10 for enabling selectively connecting up with a particular hole 8 of a container or sector of the quarantine buffers 40A, 40E, 40C. This allows for the taking of a sample of each of the predetermined amounts of used plastic material. The system may further be provided with a hopper 11a of a small pulverizer 11b for ensuring that the samples taken from the very different predetermined amounts of used plastic material, have a comparable, i.e. similar, morphology before carrying out further measurements.

A system according to the invention may further be provided with a rheology measuring system for measuring rheology properties of a sample of the predetermined amount of used plastic material to obtain rheology data. An example of such a rheology measuring system is shown in FIG. 5. The rheology measuring system may be provided with an extruder 13 for extruding the sample to an extruded sample and for measuring rheology properties. The extruder may be provided with a device for measuring the mass pressure 16 of the sample in the extruder, with a device for measuring the mass temperature 17 of the sample in the extruder, and with a device for measuring the motor torque needed for extruding the sample into an extruded sample. These process parameters are schematically represented in FIG. 5 by mass pressure 16, mass temperature 17 and motor torque 18. The data obtained can be stored in a temporary data base of control system 19. Preferably, the extruded sample is fed through a ribbon-shaped die head 14 and as such made into a strip 15.

Preferably, the system is also provided with an impurity measuring system arranged for measuring at least a number of contamination particles in an area of a predetermined size in the extruded strip 15. The measuring system may alternatively, or additionally, be arranged for measuring particle-size distribution of contamination particles in the extruded strip 15 in an area of predetermined size. Preferably, the impurity measuring system is provided with a small calender 20 to give the extruded strip a flat and consistent surface. The impurity measuring system may further comprise a visual recording device and an image analysis system, for example formed by camera 21, lighting system 22a and image processing software 22b for detecting any physical impurities on the surface of the strip, for measuring surface impurities and for classifying these impurities in size classes. The image processing software 22b will further be arranged to store these data.

It is also possible the impurity measuring system measures in the sample, extruded or not, in an area of a predetermined size. The volume and/or the area and/or the length of contamination particles. With the aid of software, a number for the degree of contamination may be obtained. When, for instance, in a predetermined area of 100 mm$^2$, three particles having each a diameter of 1 mm are found and two particles having a diameter of 3 mm are found, then the degree of contamination may be calculated as $(3\times1)+(2\times3)=9/100$ mm$^2=0.09$/mm$^2$ The system is further provided in an information carrier for carrying the rheology data and/or the impurity data and for labelling the respective in correspondence with the labelling of the predetermined amount of used plastic material. The information carrier may take any possible form. It could be the hard disc, a temporary disc, or for instance of package of information to be sent in any possible way for communicating this information about the predetermined amount of used plastic material. As these data are labelled in correspondence with the labelling of the predetermined amount of used plastic material, for instance by simply referring to the position or location of the predetermined amount of used plastic material, the system allows for providing an assembly of an amount of used plastic material and an information carrier carrying data of at least one quality property of the amount of used plastic material.

With reference again to FIG. 5, the system may be arranged for providing an encoder 23 for setting a specific length of the strip 50 for which the data need to be stored before any further processing takes place. Once impurity data are obtained from the specific length, the obtained data can be stored and processed by the control system 19. Control system 19 may compare the obtained data with predetermined data, and on that basis issue a so-called quality grade.

The system according to the embodiment of the invention may further comprise at least one blender for blending a number of predetermined amounts of used material of which at least one quality property has been determined. FIG. 6 shows schematically examples of such blenders by means of containers or of silos 26. The blender may be formed by valve 24 in FIG. 1 and FIG. 3 or one of the valves 25 in FIG. 2. This allows for release of a predetermined amount of the waste plastic material temporarily stored in a quarantine buffer for transport to container, or silo 26, as shown in FIG. 6. A buffer according to FIG. 1 will be emptied until sensor 4 detects that no longer material is present at that level. It is of course possible that predetermined amounts of used plastic material having a comparable, i.e. similar, quality, will be blended together in one of the containers or silos 26, so as to end up with a large amount of used waste material, all having the same quality. However, it may also be possible to deliberately upgrade a small predetermined amount of used plastic material, with a large predetermined amount of used plastic material having a better quality. Similarly, it will be possible to downgrade deliberately used plastic material.

Finally, it will also be possible that the system is arranged to reject used waste material, for instance, in big bag 27 (as shown in FIG. 6) if the quality is not good enough for further processing.

The invention as far as the method is concerned will now be described with reference to the drawing. The method provides for an assembly of an amount of used plastic material and an information carrier carrying data of at least one quality property of the amount of used plastic material. Such an assembly is shown in FIG. 6. Each container or silo 26 shows an amount of used plastic material of a particular grade (A, B, C, D). Each grade means that the quality property is within a predetermined range of quality properties. These containers 26 could be provided with a label, indicating the grade of the material kept in the container. Such a grade is a quality property of the amount of used plastic material kept in that container. However, it is also possible that an alternative, or additional information carrier is available at a position at a remote distance from the containers.

Figure 4A:
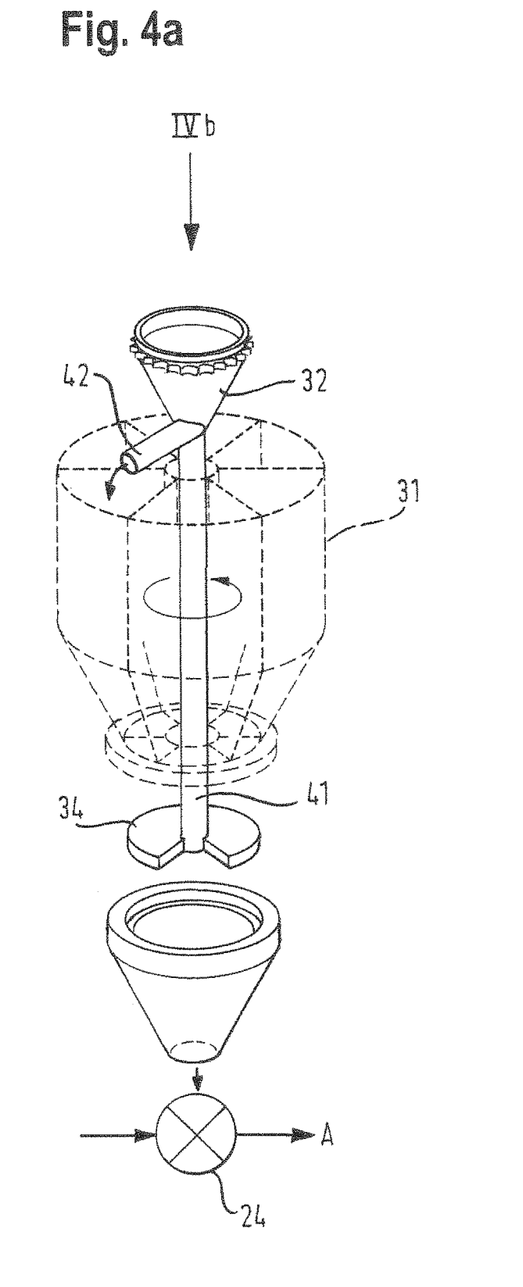
FIG. 4a shows in a more exploded view parts of the third embodiment of a system according to the invention.
Figure 4B:
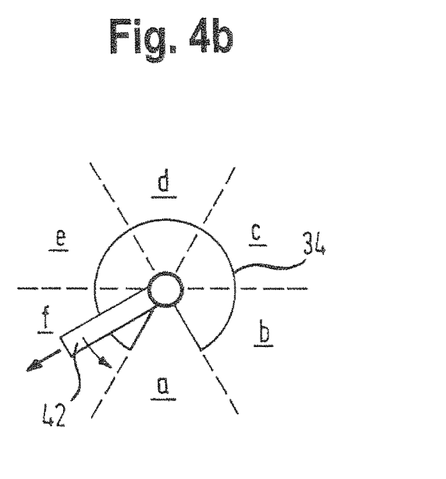

It is possible that a predetermined amount of used plastic material is isolated out of a continuous flow of used plastic material. This can in essence be done by any of the configurations shown in FIGS. 1-3 (FIG. 4a and FIG. 4b provide more detail about the configurations shown in FIG. 3). In any case, each of the one or more predetermined amounts of used plastic material is labelled. This can be done by giving it an isolated position, by registering this position for instance in the computer, by keeping the amount in a container, a plastic bag, the content of a truck, a ship, or the position in a vertical pipe or storage device.

At least one quality property is determined of one or more of the predetermined amounts of used plastic material. This is based on method steps for quality assessment. These may comprise measuring rheology properties of a sample of the predetermined amount of used plastic material to obtain rheology data.

A sample can be taken by means of pump 9, sucking away via pipe 8, from a predetermined amount of used material, a small amount of that material. This sample material can be guided via another multi-way-valve 10 into hopper 11a for pulverizing by means of pulverizer 11b. When the pulverized material has a standard particle size, it is fed into hopper 12 of small extruder 13. Whilst being extruded, mass pressure 16 is measured, mass temperature 17 is measured and motor torque 18 is measured, giving mass pressure and mass temperature of the sample as well as shear end of flow properties of the sample. These rheology data are provided on an information carrier, such as for instance a hard disk of control system 19.

Methods for quality assessment may also comprise measuring impurity properties of a sample. In the samples shown by the Figures, this comprises measuring impurity properties of the extruded sample. For this purpose, the extruded sample is calendered by a small calender 20 to give it a flat and consistent surface. A camera system with camera 21, adequate lighting 22a and image processing software 22b detects any physical impurities on the surface of the strip, measures them, classifies them in size classes and stores the so-obtained impurity data, for instance in control system 19. As such, also the impurity data are provided on an information carrier.

The information carrier is further labelled in a way which corresponds to the labelling of the predetermined amount of used plastic material, so that it is clear which data apply to which predetermined amount of used plastic material.

Measuring the impurity properties can be based on counting in the sample or in the extruded sample an area of a predetermined size the number of contamination particles in an area of a predetermined size and/or obtaining a particle size distribution of contamination particles in the sample or in the extruded sample. It is also possible to measure in the sample or in the extruded sample in an area of a predetermined size the volume and/or the area and/or the length of contamination particles. It is further possible to obtain a number for the degree of contamination. During measuring the rheology and/or impurity properties of the sample of the predetermined amount, the predetermined amount is temporarily stored in one or more buffers.

The amount of used plastic material, for instance as shown in FIG. 6, as kept in containers or silos 26, can further be micronized, to facilitate further processing of this material. The rheology data and/or the impurity data may also be expressed in terms of possible use of the amount of used plastic material. Such possible use is then based on a predetermined relationship between such use and the rheology data and/or the impurity data. It is even possible that the amount of used plastic material is provided in the form of at least one product having a shape which is different from each predetermined amount of used plastic material. In other words, the amount of used plastic material may have been turned into an end product. The quality properties of the amount of used plastic material may still apply. Such an amount of used plastic material may be provided in the form of at least one product which has a shape suitable for repeated use of that at least one product.

The method can be carried out continuously, producing small batches of predetermined material of which the quality properties are known. The sample may be reunited with the predetermined amount of material from which it was taken, or it may be rejected altogether. The method can be carried out in many different ways, not necessarily as described in this specification.

Also the system may be carried out in many different ways, not necessarily as described in this specification.

In a highly sophisticated embodiment of the invention, a predetermined amount of plastic waste material with quality properties outside a predetermined range is mixed with an amount of waste material having quality properties within that predetermined range, so that a form of "diluting" occurs. The distribution of value for a property will be over a broader range of values for that property. However, it is also possible to "purify" plastic waste material by repeatedly subjecting predetermined amounts of plastic waste material to the steps for quality assessment and narrowing the ranges for sorting material on the basis of the measured quality properties.

The assembly according to the invention can have many different embodiments. Particularly the information carrier can take any form suitable. There is no limitation in that respect. Clearly, many modifications are possible within the framework of the invention as provided by the appended claims.

The invention claimed is:

1. A method for assembling an amount of used plastic material and an information carrier carrying data of at least one quality property of the amount of used plastic material, the method comprising:
providing a predetermined amount of used plastic material from the amount of used plastic material;
labelling the predetermined amount of used plastic material;
determining at least one quality property of the predetermined amount of used plastic material by at least one of measuring rheology properties of a sample of the predetermined amount of used plastic material to obtain rheology data, and measuring impurity properties of a sample to obtain impurity data;
providing the rheology data and/or the impurity data on an information carrier; and
labelling the information carrier in a way which corresponds to the labelling of the predetermined amount of used plastic material,
wherein measuring rheology properties comprises measuring during extrusion of the sample into an extruded sample at least one of a mass pressure of the sample, a mass temperature of the sample, and at least one of a shear and flow property of the sample.

2. The method according to claim 1, wherein measuring impurity properties comprises at least one of counting in the sample or in the extruded sample in an area of a predetermined size the number of contamination particles in an area of a predetermined size, obtaining a particle size distribution of contamination particles in the sample or in the extruded sample, measuring in the sample or in the extruded sample in an area of a predetermined size at least one of a volume, an area and a length of contamination particles, and obtaining a number for the degree of contamination.

3. The method according to claim 1, wherein providing the predetermined amount of used plastic material comprises isolating a predetermined amount of used plastic material out of a continuous flow of used plastic material.

4. The method according to claim 1, further comprising storing the predetermined amount temporarily in one or more buffers during measuring at least one of rheology and impurity properties of the sample of the predetermined amount.

5. The method according to claim 1, wherein the amount of used plastic material is equal to the predetermined amount of used plastic material.

6. The method according to claim 1, wherein providing a predetermined amount of used plastic material comprises combining two or more predetermined amounts of used material, wherein for each predetermined amount of used material of the two or more predetermined amounts of used material, at least one quality property has been determined and at least one of rheology data and impurity data has been provided on the information carrier.

7. The method according to claim 6, wherein determining the at least one quality property of the predetermined amount of used plastic material comprises using the at least one of the rheology data and the impurity data on the information carrier as provided for each predetermined amount of used material of the two or more predetermined amounts of used material that are combined for providing the amount of used plastic material.

8. The method according to claim 1, wherein the rheology data and/or the impurity data are expressed in terms of a possible use of the amount of used plastic material, wherein the possible use is based on a predetermined relationship between such use and the at least one of rheology data and the impurity data.

9. The method according claim 1, wherein the amount of used plastic material is provided in the form of at least one product having a shape which is different from each predetermined amount of used plastic material.

10. A system for assembling an amount of used plastic material and an information carrier carrying data of at least one quality property of the amount of used plastic material, the system comprising:
a feeder for providing used plastic material;
at least one quantity measuring system for obtaining a predetermined amount of used plastic material and for labelling the predetermined amount of used plastic material;
at least one of a rheology measuring system for measuring rheology properties of a sample of the amount of used plastic material to obtain rheology data, and an impurity measuring system for measuring impurity properties in the sample to obtain impurity data; and an information carrier for carrying the rheology data and/or the impurity data and for labelling the respective data in correspondence with a labelling of the predetermined amount of used plastic material, wherein the rheology measuring system is arranged for extruding the sample into an extruded sample and for measuring rheology properties, the rheology properties comprising at least one of a mass pressure of the sample, a mass temperature of the sample, and at least one of a shear and flow property of the sample.

11. The system according to claim 10, wherein the impurity measuring system is arranged for measuring at least one of a number of contamination particles in an area of a predetermined size in the sample or in the extruded sample, a particle size distribution of contamination particles in the sample or in an area of a predetermined size in the extruded sample, at least one of a volume, area and length of contamination particles, and a number for a degree of contamination.

12. The system according to claim 10, wherein the impurity measuring system comprises a camera and an image analysis system.

13. The system according to claim 10, wherein the feeder forms a downstream end of a material storage system, a downstream end of a recycling processing system, or an upstream end of a production system.

14. The system according to claim 10, wherein the at least one quantity measuring system comprises one or more buffer containers.

15. The system according to claim 10, further comprising a blender for blending a number of predetermined amounts of used material of which at least one quality property has been determined.

* * * * *